United States Patent
Neuenfeldt

(10) Patent No.: US 6,626,848 B2
(45) Date of Patent: Sep. 30, 2003

(54) METHOD AND DEVICE TO REDUCE NEEDLE INSERTION FORCE

(75) Inventor: Eric Matthew Neuenfeldt, Cincinnati, OH (US)

(73) Assignee: Eric M. Neuenfeldt, Cincinnati, OH (US)

( * ) Notice: Subject to any disclaimer, the term of this patent is extended or adjusted under 35 U.S.C. 154(b) by 75 days.

(21) Appl. No.: 09/822,490

(22) Filed: Mar. 30, 2001

(65) Prior Publication Data

US 2002/0143269 A1 Oct. 3, 2002

(51) Int. Cl.[7] .............................................. A61B 10/00
(52) U.S. Cl. ........................ 600/564; 600/567; 600/568; 606/167
(58) Field of Search .................................. 600/562, 564, 600/566, 567, 568; 606/167, 170, 171; 604/19, 22; 112/2, 189, 1, 192–195

(56) References Cited

U.S. PATENT DOCUMENTS

| | | | |
|---|---|---|---|
| 4,306,570 A | | 12/1981 | Matthews |
| 4,667,684 A | | 5/1987 | Leigh |
| 4,919,146 A | | 4/1990 | Rhinehart et al. |
| 4,936,845 A | * | 6/1990 | Stevens ........................ 604/22 |
| 5,241,969 A | | 9/1993 | Carson et al. |
| 5,249,583 A | * | 10/1993 | Mallaby ...................... 600/567 |
| 5,251,641 A | | 10/1993 | Xavier |
| 5,476,102 A | * | 12/1995 | Como et al. ................. 600/567 |
| 5,769,086 A | * | 6/1998 | Ritchart et al. ............. 600/566 |
| 5,830,219 A | * | 11/1998 | Bird et al. ................... 606/130 |
| 6,022,324 A | | 2/2000 | Skinner |
| 6,083,176 A | | 7/2000 | Terwillger |
| 6,120,462 A | * | 9/2000 | Hibner et al. ............... 600/566 |
| 6,176,865 B1 | * | 1/2001 | Mauze et al. ............... 606/171 |
| 6,332,871 B1 | * | 12/2001 | Douglas et al. ............. 600/583 |
| 6,361,504 B1 | * | 3/2002 | Shin ........................... 600/562 |

* cited by examiner

Primary Examiner—Charles A Marmor, II

(57) ABSTRACT

The present invention relates to devices and methods to reduce the insertion force of a medical needle using reciprocal rotation motion about the longitudinal axis. The device of the invention converts continuous rotational motion to reciprocal rotational motion for the beveled needle. A needle using reciprocal rotational motion creates a slit in the tissue, sufficient in size to equal the maximum circumference of the needle prior to insertion of the needle. The insertion force will decrease as the speed of the reciprocal rotational motion increases until a steady state insertion force is achieved.

14 Claims, 5 Drawing Sheets

METHOD AND DEVICE TO REDUCE NEEDLE INSERTION FORCE

FIELD OF THE INVENTION

The present invention relates in general to devices and methods to reduce the insertion force of medical needles, biopsy needles, trocars, cutters and introducers into tissue, and more specifically, to needle insertion devices and methods employing reciprocating rotational motion.

BACKGROUND

The testing and histological analysis of tissue samples is common practice in the diagnosis and treatment of patients suspected of cancerous tumors, pre-malignant masses and other diseases or disorders. For the physician to arrive at a conclusive tissue diagnosis, an intact tissue characterization of the whole lesion or organ is required. Traditionally, open surgery was necessary to locate, identify and remove the lesion or obtain a tissue specimen. With the introduction of medical imaging equipment such as x-rays, fluoroscopy, computed tomography, ultrasound, nuclear medicine, and magnetic resonance imaging, identification of abnormalities within the body are possible. However, conclusive tissue diagnosis still requires obtaining an adequate tissue specimen utilizing open surgery or biopsy to characterize the histology of the lesion or organ.

Biopsy may be done using either an open or percutaneous technique. Open biopsy techniques are either an excisional biopsy to remove the entire mass or incisional biopsy to remove portions of the mass. Common percutaneous biopsy techniques include fine needle aspiration (FNA) or core biopsy.

Open surgical biopsies have many disadvantages. Procedure costs are high and can be traumatic or potentially disfiguring to the patient. The inherent risks of open surgery include mortality due to use of anesthesia and morbidity due to bleeding or infection. Endoscopic surgery has reduced the disfigurement, expense and associated risk of open surgery. However, endoscopic surgery presents drawbacks. It is highly site selective, requiring special surgical instruments. Therefore, less invasive alternatives such as FNA or Core biopsy are sought by the healthcare industry.

With FNA biopsy, individual cells are collected for cytological examination using a 20 to 26 gauge needle attached to a syringe. To begin the FNA procedure the needle is manually inserted though the skin to the target lesion or organ. Once the needle is inserted into the lesion or organ, a vacuum is created to aspirate cells into the lumen of the needle. The needle may be advanced and retracted several times to obtain cells from multiple locations within the lesion or organ.

U.S. Pat. No. 5,241,969 to Carson, et al. ('969) describes a fine needle aspiration device designed for use with standard needles and disposable syringes to obtain cells for the diagnosis of cancer and other pathological processes. The '969 patent discloses a fine needle having an internal diameter less than 0.5 millimeters is inserted through the skin into a palpable mass and a vacuum is applied to aspirate cells from the mass. The cells are cut free by moving the needle proximally and distally allowing the vacuum to aspirate the cells into the barrel of the syringe. The device includes an extended stabilizing ring to control the depth of needle penetration and to protect the user from needle stick accidents.

Core biopsies typically utilize 14 to 18 gauge needles or cannula to obtain a column-like sample of tissue. This technique will generally harvest a larger specimen or cylindrical cross-section of tissue often preserving the tissue architecture. Larger intact specimens from core biopsy are more suitable for histological evaluation. The type of biopsy selected by the physician depends on the circumstances with respect to the patient and upon the skill and degree of experience of the operator with FNA biopsy. No single technique is suitable for all cases. However, more core biopsy procedures are performed than FNA biopsy procedures because of higher diagnostic accuracy.

U.S. Pat. No. 5,251,641 to Xavier ('641) describes a biopsy needle for extracting human tissue specimens. In '641, the biopsy needle contains a rotating and axially removable inner cannula housed within an outer cannula in the form of a penetrating needle. The needle provides a conical piercing tip that is manually inserted into the skin through the mass by applying forward pressure. As the needle tip reaches the periphery of the specimen, the inner cannula is rotated counterclockwise 180-degrees to core a tissue sample through coextensive open channels in the inner and outer cannulas. The specimen is isolated by rotating the inner cannula clockwise 180-degrees to perform a transverse cut of the tissue and entrapping the tissue within an open distal chamber of the needle.

Despite the advantages of needle or core biopsy over open surgery, some inherent risks apply. Needle biopsy can cause post-surgical trauma to patients such as hematoma, bleeding, pneumothorax or hematuria. Wound infection is also a post-operative risk of needle or core biopsy. These complications usually relate to the needle size used for the procedure or random depth control of the needle tip during manual operation.

Both FNA and core biopsy devices have a number of disadvantages. FNA biopsy may occasionally provide an inadequate quantity or non-diagnostic cell sample. Therefore, the techniques and devices used for large core biopsy have a higher degree of acceptance than FNA devices and techniques. However, due to larger gauge needle size coupled with the need for higher insertion forces and acceleration of core biopsy, the procedure is more invasive, painful and traumatic. Additionally, core biopsy needles have been known to not penetrate dense tissue leading to increased risk of forming hematomas, swelling, and damage to surrounding tissue or structures. Due to the higher insertion forces of core biopsy needles, several devices are used to propel the needle with considerable force and speed in order to pierce the lesion and collect the specimen. These devices include biopsy guns, automated core biopsy devices (ACBD), manual and motorized devices capable of rotating needles.

U.S. Pat. No. 6,022,324 to Skinner ('324) describes a biopsy gun and needle for taking bone biopsy or soft tissue biopsy samples. In '324, the biopsy gun contains a firing mechanism for firing the biopsy needle; a cradle that securely holds the biopsy needle with an attached disposable syringe having a plunger; and a triggering mechanism. When the firing mechanism is actuated, the spring loaded cradle together with the biopsy needle move in forward stroke striking the target tissue organ causing the first tissue sample to be cored off into the needle. The syringe is then used to obtain a second tissue sample using a vacuum created when the plunger is maintained in a rearward position while the syringe is fired forward.

U.S. Pat. No. 4,667,684 to Leigh ('684) describes a biopsy device for single handed usage by the medical practitioner for obtaining a specimen of tissue, incorporating a reciprocal moving stylet within a cannula. The '684 patent discloses a pistol grip handle providing single hand insertion control of the stylet and cannula into the body along the means for guiding and controlling the reciprocal movement of the stylet and cannula. A specimen is obtained in the notch of the stylet by releasing the trigger mechanism thereby, allowing the spring loaded cannula to advance through the target tissue. A stop mechanism limits the cannula stroke in order to prevent inadvertent penetration of the stylet into the patient.

U.S. Pat. No. 6,083,176 to Terwilliger ('176) describes an automated biopsy needle handle that allows for the insertion of a needle set. In '176, the needle set is an integral unit and consists of an outer hollow cannula and an inner pointed tip stylet. In operation, the stylet and the cannula are inserted into a patient near the biopsy area. The stylet is manually advanced into the biopsy area until the operator engages the thumb activated, spring loaded, mechanism to pierce the tissue. The cannula is then triggered by firing of the stylet and automatically urged forward so the tissue is severed and captured in the notch of the stylet. The cannula is advanced to capture the sample within the notch of the stylet. This device is capable of taking multiple samples.

U.S. Pat. No. 4,919,146 to Rhinehart, et al. ('146) describes a biopsy device for obtaining tissue samples from the body utilizing drilling and aspirating techniques to obtain samples for cytologic and histologic evaluation. The '146 patent discloses a rotation energy element coupled with a drill/plunger component provides rotational motion to a cutting tip. In operation, the tissue to be sampled is manually punctured by a standard two piece biopsy needle. Rotational energy is imparted to the drill bit plunger component causing the tissue to be accumulated in the cutting tip. A vacuum is created to cause the sample to be aspirated into the cannula syringe.

U.S. Pat. No. 4,306,570 to Matthews ('570) describes a counter rotating biopsy needle comprising two counter-rotating tubes having oppositely facing sawteeth formed on the distal ends thereof. In '570, a gear system transmits a driving force to the tubes, causing the counter-rotation that permits the sawteeth to act in a cutting manner for soft tissue. Use of an outer cannula allows safe insertion of the needle to the location of the desired sample, and various grasping means are used to extract the sample core.

The requirements of the patient, physician and the pathologist dictate the need for alternative methods and devices for controlling the insertion of the biopsy needle into the body to the target site. It would be advantageous to reduce the insertion force of the needle or cannula. This would allow the operator to have greater control of the needle position along with sufficient force to pierce the lesion or organ with minimal acceleration and needle diameter.

SUMMARY OF THE INVENTION

The present invention provides an improved method and device for reducing the insertion force of needles into tissue. The present invention provides the means to rotate the needle in reciprocal motion about the longitudinal axis. The reciprocal rotational motion utilized in the present invention allows for lower insertion forces of needles into target tissue.

One aspect of the present invention provides a device to convert continuous directional 360-degree rotational motion of a first shaft, into reciprocal rotational motion of 180 degrees about the longitudinal axis of a second shaft. The reciprocal rotation motion of the second shaft is communicated directly to the needle resulting in the beveled tip of the needle having the same reciprocal rotational motion. During normal operation, a motorized source provides the continuous directional 360-degree rotational motion and means for communicating with the first shaft. The operator would select the rotational speed of the motor and in turn, the reciprocal rotational speed of the needle tip, depending on the desired insertion force of the needle by using a speed controller in communication with the motor. The operator would also have the option of no needle tip rotation. During insertion into the patient's body, the beveled tip of the needle with reciprocal rotational motion would create an incision in the tissue sufficient in size to equal the circumference of the needle.

In an alternative embodiment of the present invention, continuous directional 360-degree rotational motion of the first shaft is converted into an operator selectable reciprocal rotational motion between 1 and 360 degrees for the second shaft. The needle, by means of direct communications with the second shaft, would have the same reciprocal rotational motion and degrees of reciprocal rotation delivered to the tip of the needle. During normal use, the operator would have the option of selecting rotational speed by means of a speed controller.

In another embodiment of the present invention, continuous directional 360-degree rotational motion of the first shaft is converted into an operator selectable reciprocal rotational motion between 1 and 360 degrees or continuous rotational motion for the second shaft. The needle, by means of direct communications with the second shaft, would have the same rotational motion and degrees of rotation delivered to the tip of the distal end of the needle. During normal use, the operator would still have the option of selecting rotational speed by means of a speed controller.

In yet another embodiment of the present invention, a cable connector is attached between the device and the needle to extend the length between the device and the needle. The cable connector would communicate the reciprocal rotation motion to the needle.

BRIEF DESCRIPTION OF THE DRAWINGS

The invention and methods of operations may be better understood in relation to the following figures, wherein.

DETAILED DESCRIPTION OF THE INVENTION

Figure 1:
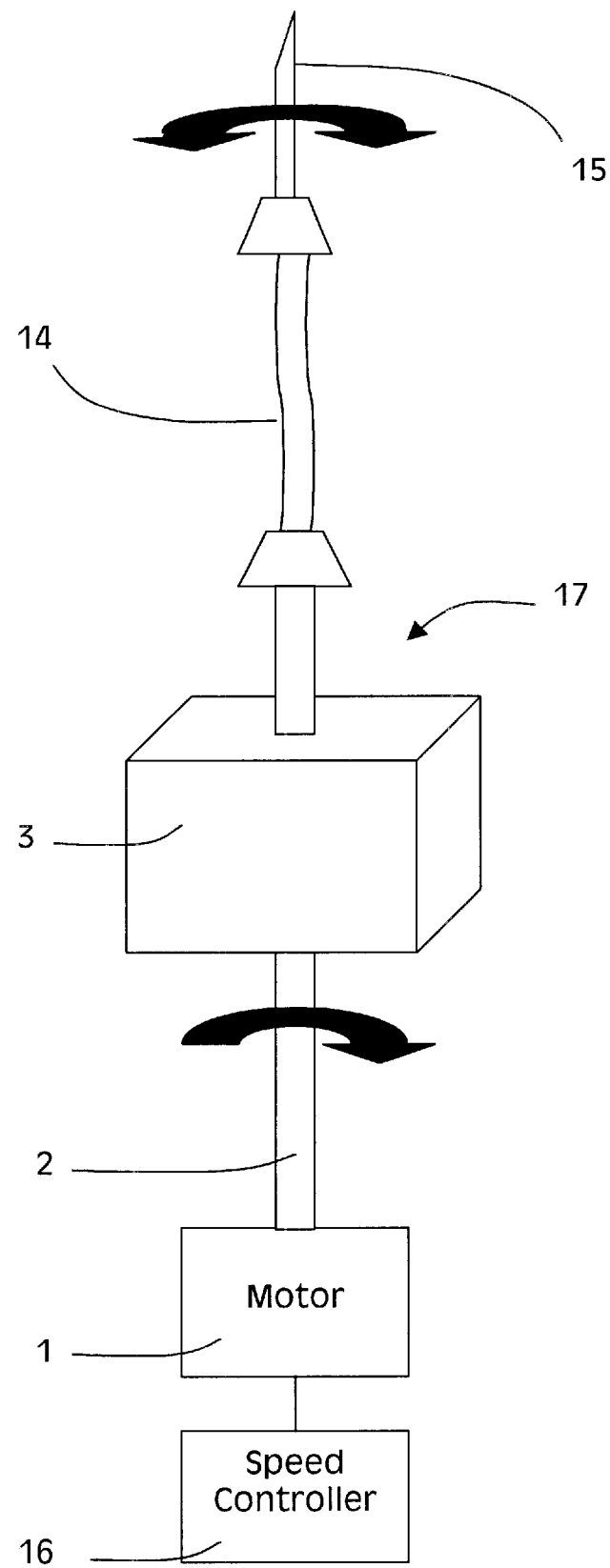
FIG. 1 is a perspective view of the reciprocal rotational motion converter shown with a motorized rotational motion source, speed controller, rotational cable and beveled needle.

In one aspect of the present invention, FIG. 1 illustrates the biopsy system 17 generating the reciprocal motion of the beveled needle 15 to reduce the insertion force of the biopsy needle into the target tissue site. As used herein, the term needle includes needles of all types, trocars, introducers, and cutters designed to penetrate tissue. The biopsy system 17 includes rotation converter device 3 with a motor 1, and speed controller 16, in communication with a needle 15 via rotational cable 14. As shown, the motor 1 provides continuous rotational motion via the motors shaft 2 to the rotational converter 3. In turn, the rotational converter 3 transforms 360 degrees of rotational motion to reciprocal rotational motion in a range from 1-degree to 360-degrees. A rotational cable 14 extends the length between the rotational converter 3 and needle 15. The speed controller 16 controls the revolutions per minute out of the motor shaft 2. The reciprocal motion of the needle 15 will aid the operator to reduce the needle insertion force into the target site.

Figure 2:
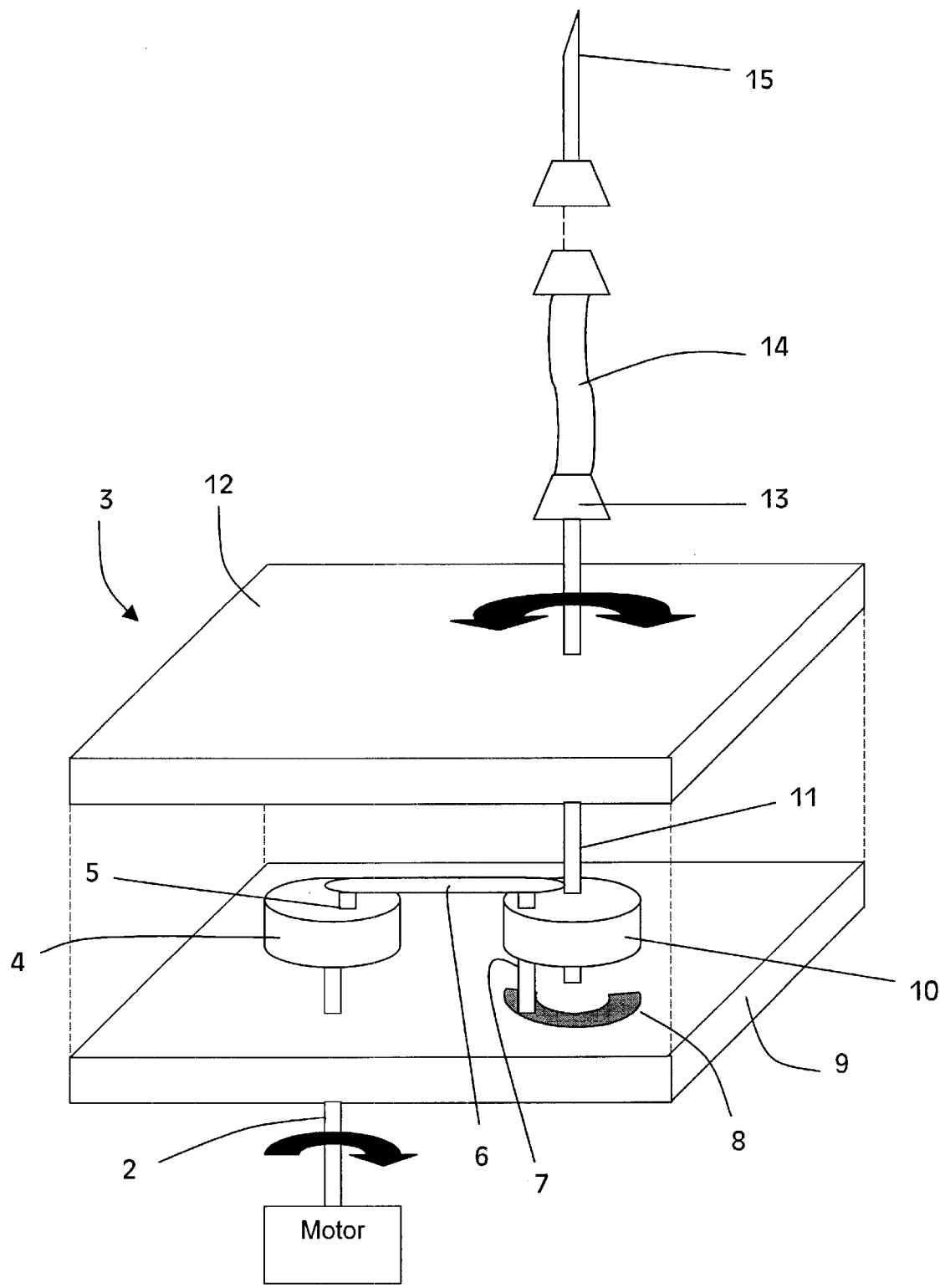
FIG. 2 is a cut-away perspective view of the device to convert rotational motion into reciprocal rotational motion.

In FIG. 2, there is illustrated a cut-away perspective view detailing the rotational converter 3. The motor shaft 2 is in direct communication with the 360-degree rotation wheel 4 within the rotation converter 3. A connector bar 6 links the 360 degree rotation wheel 4 with the 180 degree rotational wheel 10. The connector bar 6 is attached to the 360 degree rotation wheel 4 with a connector pin 5. The opposing end of connector bar 6 attaches to 180 degree rotation wheel 10 using the slot pin 7, which is in communication with 180 degree slot 8 mounted in the lower plate 9. The 180-degree slot 8, slot pin 7 and 180-degree rotation wheel 10 provides the means to convert continuous directional motion to reciprocal rotational motion. The 180-degree wheel 10 is in communication with a rotation shaft 11 and in turn the cable connector 13. This link will provide about 180 degrees of reciprocal rotation motion about the axis of the cable connector 13. The 360-degree rotation wheel 4, connection pin 5, connector bar 6, and the exposed portion of slot pin 7 are contained within the lower plate 9 and upper plate 12. A rotational cable 14 contains a shaft capable of communicating the reciprocal rotational motion to the needle 15. During operation, needle 15 connected to the distal end of the rotational cable 14 will move with the same rotational motion and speed as the shaft of the rotational cable 14.

In a further embodiment, the 180 degree slot 8 may vary from 1 degree to 360 degrees about the axis of the rotational shaft 11. This will result in a needle 15, rotational cable 14, and rotational wheel 10 with similar degrees of reciprocal rotational motion as the new width of slot 8.

In a further embodiment, the rotational cable 14 may be eliminated. The needle 15 would be connected directly to the cable connector 13 and in communication with the rotational shaft 11.

In a further embodiment, needle 15 may be, for example, a trocar, a sharp introducer, or a beveled cutter.

Figure 4:
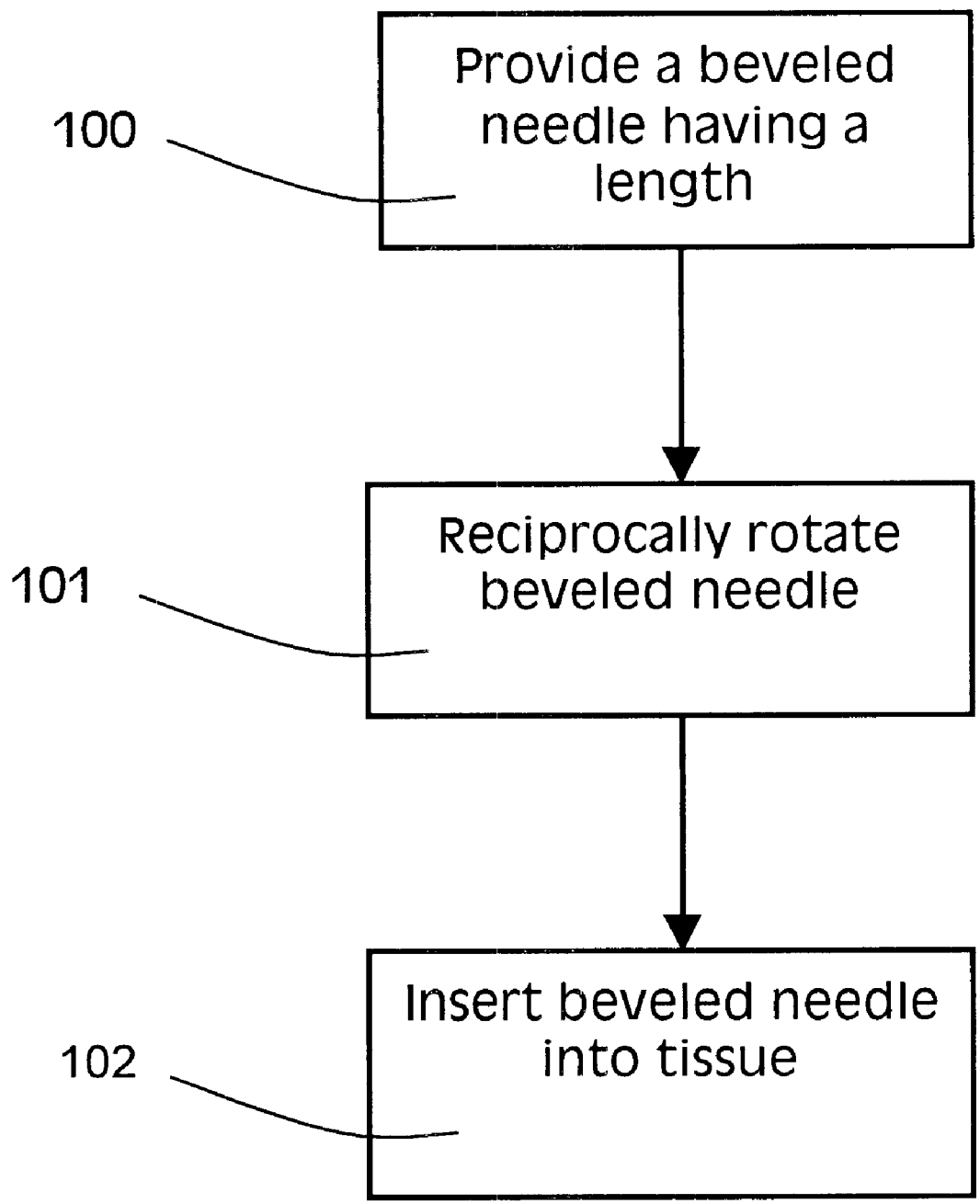
FIG. 4 is a flowchart of the method to reduce the insertion force of a needle or cannula.

One advantage of this invention is to use needle 15 with reciprocal rotation motion about the longitudinal axis of the needle shaft to lower the insertion force for the operator, therefore improving control and placement of needle 15 in tissue. A flow chart of the method of the present invention is shown in FIG. 4. A method of introducing a needle into tissue according to the present invention includes the following steps;

a) providing a beveled needle having a length, the length defining an axis, designated step 100 in FIG. 4;

b) reciprocally rotating the beveled needle about its axis, wherein the rotation is within the range of about 1 degree to about 360 degrees, designated step 101; and c) inserting the beveled needle into tissue, designated step 102.

Alternate aspects of a method according to the present invention may include one or more of the following variations:

d) in step b above, reciprocal rotation is in the range of 45 to 360 degrees; and e) in step b above, reciprocal rotational motion of the needle is from 1 to 4000 cycles per second.

Figure 5:
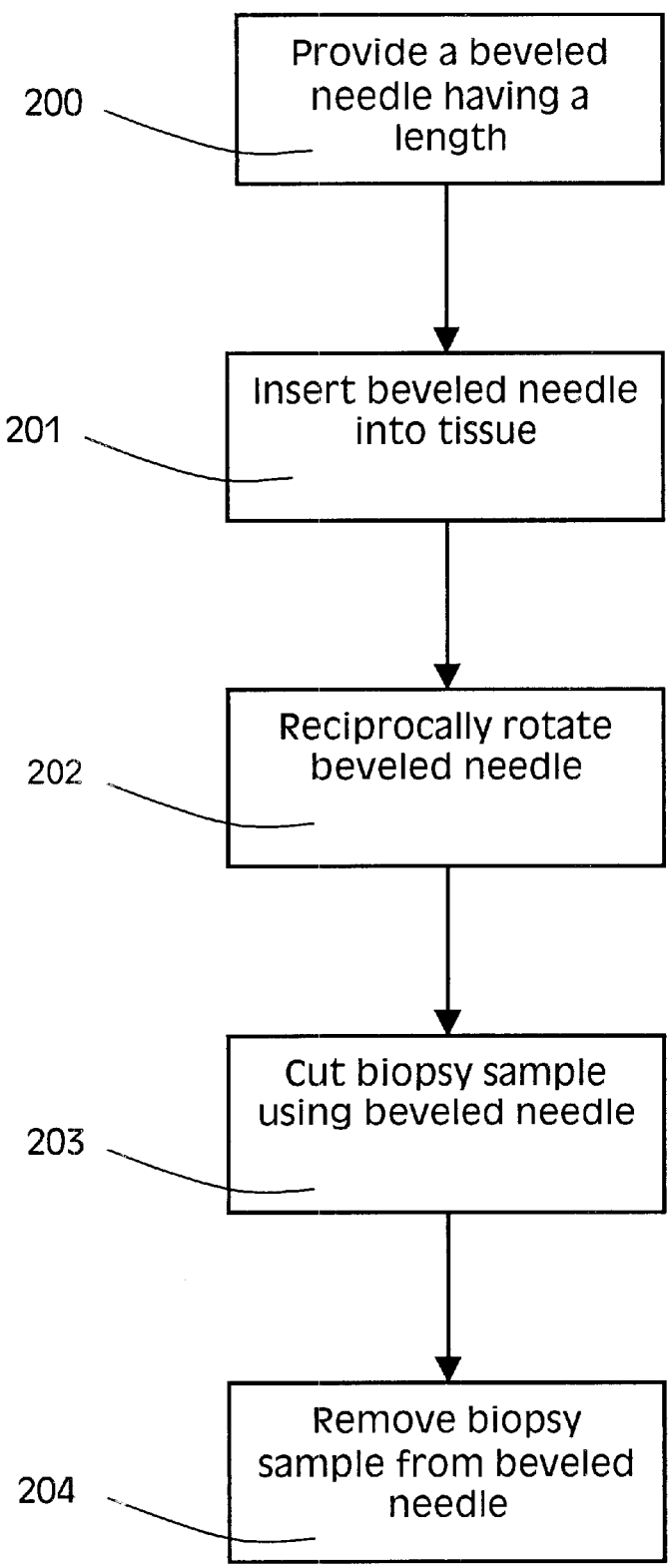
FIG. 5 is a flowchart of an alternative method to reduce the insertion force of a needle or cannula.

A flow chart of an alternative method of the present invention is shown in FIG. 5. The alternative method of introducing a needle into tissue according to the present invention includes the following steps;

a) providing a beveled needle having a length, the length defining an axis, designated step 200 in FIG. 5;

b) inserting the beveled needle into tissue, designated step 201;

c) reciprocally rotating the beveled needle about its axis, wherein the rotation is within the range of about 1 degree to about 360 degrees, designated step 202;

f) cutting a biopsy sample, designated step 203; and g) removing the biopsy sample from the beveled needle, designated step 204.

Example of Insertion Force Study

This study demonstrates that the use of reciprocal rotating motion about the longitudinal shaft of a beveled needle will reduce the insertion force of the needle.

Materials and Methods

A rotational converter device was constructed to convert continuous 360 degrees of rotational motion of an input shaft to reciprocal rotational motion of 180 degrees of an output shaft. The $1^{st}$ disk or 360 degree-rotation wheel was made with a diameter of 0.875 inches and height of 0.125 inches. A hole with a diameter of 0.125 inches was drilled 0.250 inches away from the center axis of the $1^{st}$ disk and a hole with a diameter of 0.125 inches was drilled in the center of the disk. The first shaft or motor shaft was constructed with a diameter of 0.125 inches and a length of 1.250 inches. The $1^{st}$ shaft was inserted in the center hole of the 1st disk. The $2^{nd}$ disk or 180 degree-rotational wheel was made with the same dimensions and holes as the $1^{st}$ disk. A $2^{nd}$ shaft or rotation shaft with a diameter of 0.125 inches and a length of 1.250 inches was made with a male Luer connector on one end. The end of the $2^{nd}$ shaft with a diameter of 0.125 inches was inserted in the center hole of the $2^{nd}$ disk. A connector bar with a length of 1.360 inches, a height of 0.125 inches in height, and width of 0.375 inches was made. The ends were curved to a radius of 0.1875 inches and a hole with a diameter of 0.125 inches was drilled along mid line of the connector centered at the point of equal radius from the curved ends. A notch measuring 0.600 inches in length and 0.200 inches in width was cut out 0.330 inches from one end of the connector bar. One end of the connector bar was attached to the $1^{st}$ disk using the hole with a diameter of 0.125 inches, and a 0.125 diameter pin with a height of 0.250 inches. The other notched end of the connector bar was attached the $2^{nd}$ disk with the notch of the connector bar facing inward to the 0.125 inch diameter hole using a 0.125 inch diameter pin, 0.375 inches in height. This placement of the notch would allow for clearance around the $2^{nd}$ shaft during use. A lower plate measuring 3.115 inches in length, 2.000 inches in width, and 0.500 inches in height was built. A hole 0.128 inches in diameter was drilled through the lower plate along the longitudinal mid line, 1.000 inches from the edge. A second hole with a diameter of 0.128 inches was drilled through the lower plate along the longitudinal mid line, 2.000 inches from the edge. An arc groove with an angle of 180 degrees was cut into the lower plate, with a depth of 0.200 inches and a width of 0.135 inches. The center of the groove was placed 0.250 inches from the center of first hole and ends of groove were of equal distance to the mid line of the lower plate. An upper plate was built with a length of 3.115 inches, a width of 2.000 inches and a height of 0.216 inches. A hole with a diameter of 0.128 inches was drilled through the upper plate along the longitudinal mid line, 1.000 inches from the edge. The rotation converter was assembled using spacers with a height of 0.300 inches and placed between the upper and lower plates.

Once the rotational converter was built, the input shaft of the rotation converter was mounted to the motor shaft of a tool with a rated output range of 5,000 to 25,000 revolutions per minute. A suitable tool would be a Multipro DREMEL, a trademark name of Dremel Corporation, Racine, Wis. A variac-speed controller was coupled to the Multipro DREMEL tool to control supply voltage and in turn the continuous rotation speed output of the motor shaft of the Multipro DREMEL tool. To obtain proper rotation of the motor shaft of the Multipro DREMEL tool, a piece of florescent tape was mounted to the motor shaft of the Multipro DREMEL tool. An infrared sensor collected revolutions from the florescent tape and displayed revolutions per minutes (or rotations per minute) on a tachometer. One rotation per minute as displayed on the tachometer represented one complete cycle of reciprocal motion of the needle about the longitudinal axis.

Needles selected for experimentation were dual bevel tipped I.V. needles manufactured by Sherwood Medical Corporation, St. Louis, Mo. The needles sizes used were 16, 20, 22, and 25 gauge with 1 inch shaft lengths. The I.V. needles met American National Standards Institute Luer Lock connector requirements.

Synthetic plastic sheeting was used to simulate soft tissue for all insertion force testing. A suitable synthetic plastic material is PORVAIR, a trademark name of PORVAIR Advanced Material, Inc., of Hendersonville, N.C.

Test Procedure

A motorized tensile tester was outfitted with a two pound—load cell and set at a rate of 15 inches per minute. A suitable motorized tensile tester would be an INSTRON, a trademark name from INSTRON Corporation, Canton, Mass. The PORVAIR sheeting was mounted to a fixture between two plates, each containing a hole with a diameter of 1 inch to support the test material during needle insertion. The supporting plate fixture was then bolted to the motion arm of the INSTRON tester. A clamping fixture attached the Multipro DREMEL tool and rotational converter to the base of the INSTRON tester. The infrared sensor was mounted into position and electrically connected to the tachometer to measure revolutions per minute of the Multipro DREMEL tool. A Variac-Speed controller was coupled to the Multipro DREMEL tool to control supply voltage and in turn the continuous rotation speed output of the motor shaft of the Multipro DREMEL tool.

Once the INSTRON tester was set up, a 16 gauge needle was attached to the output connector the rotational converter. The motion arm of the INSTRON tester was advanced to position the needle tip approximately 0.50 inches from the mounted Synthetic PORVAIR sheeting. A control group measurement was taken at zero rotations per minute for the needle size. Needle gauge size, rotations per minute, insertion force, peak insertion force and needle position were recorded for each control and test sample. Test group data were recorded for rotational speeds of approximately 600, 900, 1800, 2500, 3000, 4000 and 4200 rotations per minute. The testing procedure was repeated for the 20, 22, and 25 gauge needle size test groups. Peak Insertion Force, rotational speed and needle size were plotted and analyzed.

Figure 3:
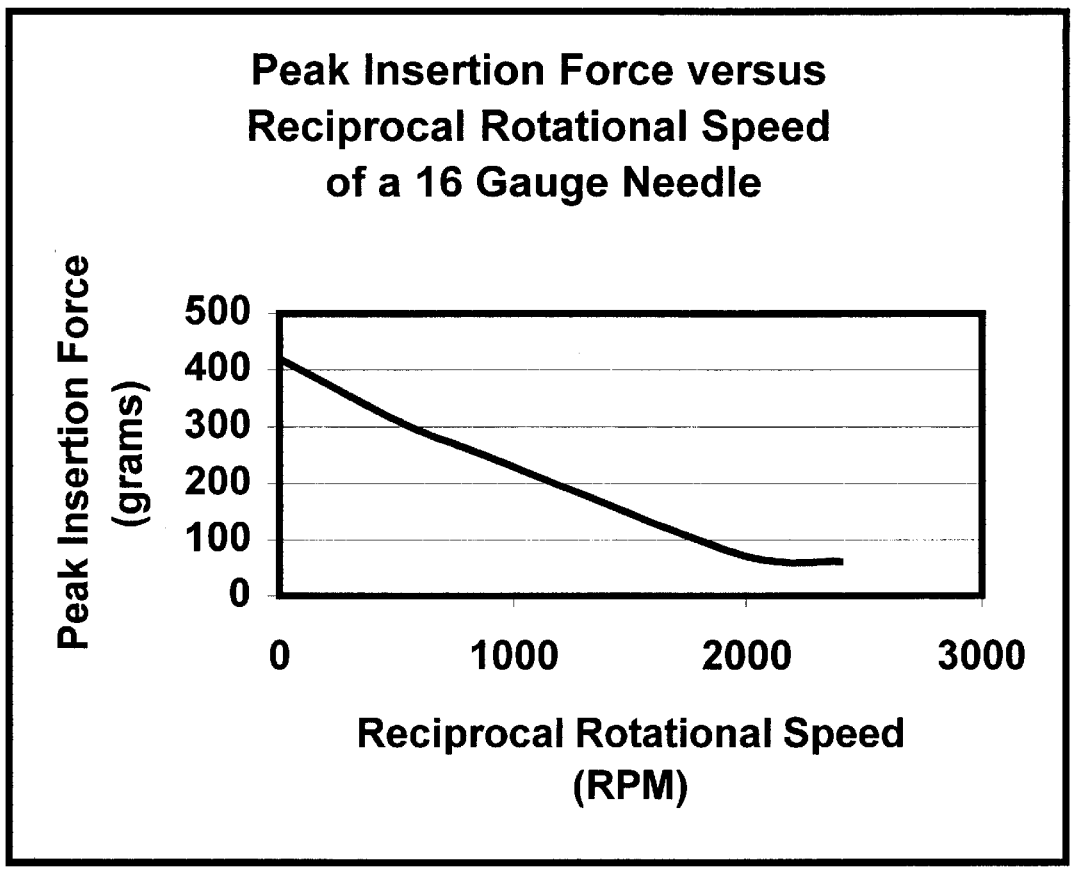
FIG. 3 is a plot of Peak Insertion Force versus Rotational Speed for a 16 gauge double bevel I.V. needle.

FIG. 3 shows a plot of Peak Insertion Force versus Rotational Speed for a 16 gauge needle. This plot demonstrates that peak needle insertion force decreases as rotational speed or reciprocal rotational speed of the needle increases.

While preferred embodiments of the present invention have been shown and described herein, it will be obvious to those skilled in the art that such embodiments are provided by way of example only. Numerous variations, changes and substitutions will occur to those skilled in the art without departing from the invention. Accordingly, it is intended that the invention be limited only by the spirit and scope of the claims.

The present invention may be better understood with the reference to the accompanying example intended for purposes of illustration only and should not be construed to limit the scope of the invention, as defined in the claims appended hereto.

What is claimed is:

1. A device for converting continuous rotation of a shaft into reciprocal rotational motion of a beveled needle comprising:
   a) a first shaft having a first end, a second end and a length defining a first shaft axis therebetween, wherein said first end is adapted to connect to a motor for imparting a continuous rotation on said first shaft about said first shaft axis;
   b) a first disk rigidly attached to said second end of said first shaft, said first disk comprising an attachment pin formed on a side thereof;
   c) a second shaft having a first end, a second end and a length defining a second shaft axis therebetween, wherein said second end of said second shaft is connected to a beveled needle;
   d) a second disk rigidly attached to said first end of said second shaft, said second disk comprising an attachment pin formed on a side thereof;
   e) a connector arm having a first end and a second end, wherein said first end of said connector arm being operatively connected to said attachment pin of said first disk and said second end of said connector arm being operatively connected to said attachment pin of said second disk; and
   f) translating means for providing said reciprocal rotational motion, in communication with said second disk, for converting said continuous rotational motion of said first shaft about said first shaft axis into said reciprocal rotational motion of said second shaft about said second shaft axis.

2. The device according to claim 1, wherein said translating means for providing said reciprocal rotational motion is adjustable within a range of 1 degree to 360 degrees.

3. The device according to claim 1, wherein said translating means for providing said reciprocal rotational motion is adjustable within a range of 45 degrees to 360 degrees.

4. The device according to claim 1, wherein a cable with a rotating shaft is connected to the second end of said second shaft to extend the length of said second shaft.

5. A method to reduce insertion force of a dual beveled needle into tissue, comprising the steps of:
   a) providing a device including a dual beveled needle having a length, said length defining an axis, and means for converting continuous rotation of a shaft into reciprocal rotational motion of said dual beveled needle;
   b) operating said device to provide said dual beveled needle with a reciprocal rotational motion about said axis of said dual beveled needle, wherein said reciprocal rotational motion is within the range of about 1 degree to about 360 degrees; and c) inserting said dual beveled needle into tissue;

where in the insertion force of said dual beveled needle decreases as the speed of said reciprocal rotational motion increases.

6. The method of claim 5, wherein in step b, said reciprocal rotational motion of said dual beveled needle is in the range of 45 to 360 degrees.

7. The method of claim 5, wherein the speed of said reciprocal rotational motion of said dual beveled needle is from 1 to 4000 cycles per second.

8. The method of claim 5, wherein the speed of said reciprocal rotational motion of said dual beveled needle is greater than 1 cycle per second.

9. The method of claim 5, further comprising the steps of:

d) cutting a biopsy sample with said dual beveled needle; and e) removing said biopsy sample from said dual beveled needle.

10. A method to reduce insertion force of a dual beveled needle into tissue, comprising the steps of:

a) providing a device including a dual beveled needle having a length, said length defining an axis, and means for converting continuous rotation of a shaft into reciprocal rotational motion of said dual beveled needle;

b) inserting said dual beveled needle into tissue; and c) operating said device to provide said dual beveled needle with a reciprocal rotational motion about said axis of said dual beveled needle, wherein said reciprocal rotational motion is within the range of about 1 degree to about 360 degrees, and wherein the insertion force of the dual beveled needle decreases as the speed of the reciprocal rotational motion increases.

11. The method of claim 10, wherein in step c, said reciprocal rotational motion is in the range of 45 to 360 degrees.

12. The method of claim 10, wherein the speed of said reciprocal rotational motion of said dual beveled needle is from 1 to 4000 cycles per second.

13. The method of claim 10, wherein the speed of said reciprocal rotational motion of said dual beveled needle is greater than 1 cycle per second.

14. The method of claim 10, further comprising the steps of:

d) cutting a biopsy sample with said dual beveled needle; and e) removing said biopsy sample from said dual beveled needle.

* * * * *